United States Patent [19]
Hasseberg et al.

[11] Patent Number: 6,008,409
[45] Date of Patent: Dec. 28, 1999

[54] METHOD FOR OBTAINING 2-HYDROXY-4-METHYLTHIOBUTYRIC ACID (MHA) WHICH IS STABLE IN STORAGE

[75] Inventors: Hans-Albrechl Hasseberg, Gründau; Hans-Joachim Hasselbach, Gelnhausem; Klaus Huthmacher, Gelnhausen; Volker Häfner, Langenselbold; Harald Heinzel, Frankfurt; Axel Ronneburg, Hanau, all of Germany

[73] Assignee: Degussa Aktiengesellschaft, Frankfurt, Germany

[21] Appl. No.: 08/999,000

[22] Filed: Dec. 29, 1997

[30] Foreign Application Priority Data

Dec. 27, 1996 [DE] Germany ............... 196 54 485

[51] Int. Cl.$^6$ .................................................. C07C 315/00
[52] U.S. Cl. ............................................ 562/581; 560/152
[58] Field of Search ............................. 562/581; 560/152

[56] References Cited

PUBLICATIONS

CA 79: 52804 (1973).
CA 109: 54325 (1987).

*Primary Examiner*—Paul J. Killos
*Attorney, Agent, or Firm*—Pillsbury Madison & Sutro, LLP

[57] ABSTRACT

A method for obtaining 2-hydroxy-4-methylthiobutyric acid (methionine-hydroxy analog, MHA) in primarily free form which is stable in storage by distilling a product solution containing MHA and by producing MHA product mixtures with improved storage stability from such a distillate. The distillate can be produced directly starting from MHA raw products from any MHA production process, which can optionally also contain solvent or water. The starting material may also be a commercial MHA product.

12 Claims, 12 Drawing Sheets

METHOD FOR OBTAINING 2-HYDROXY-4-METHYLTHIOBUTYRIC ACID (MHA) WHICH IS STABLE IN STORAGE

FIELD OF THE INVENTION

The invention relates to a method for obtaining 2-hydroxy-4-methylthiobutyric acid (methionine-hydroxy analog, MHA) in primarily free form which is stable in storage, by distilling a product solution containing MHA and by producing MHA product mixtures with improved storage stability from such a distillate. The distillate can be produced directly starting from MHA raw products from any MHA production process, which can optionally also contain solvent or water, as well as starting from a commercial MHA product.

BACKGROUND OF THE INVENTION

MHA is the hydroxy analog of the essential amino acid methionine in racemic form and is, like the latter, an important additive in animal nutrition, especially in poultry raising, but also in many other areas. In addition, MHA has also been used pharmaceutically in the form of its calcium salt to treat renal insufficiency as a substitute for dialysis treatment or to supplement dialysis, as is indicated e.g. in DE-OS 25 31 299.

MHA is usually used in animal nutrition in the form of its aqueous concentrates which also contain, in addition to the monomer, a certain amount of oligomers, primarily the di- and trimeric linear ester acids. The content of these oligomers is a function of the production conditions and also of the concentration selected. However, it is desirable to keep their percentage as low as possible on account of their lower nutritive efficiency of action in comparison to monomeric MHA and on account of the unfavorable influence on the flow properties as a consequence of the elevation of the viscosity. Commercial formulations have, at a total concentration of 88–90% by weight, up to 24% by weight, corresponding to approximately 27 molar %, in sum of oligomers, corresponding to a monomer/oligomer/ratio of approximately 3:1.

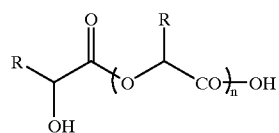

The synthesis pathway which is exclusively used industrially starts from methylmercaptopropionaldehyde (MMP), which is converted by HCN addition into the corresponding cyanohydrin (MMP-CH), which is then, catalyzed with sulfuric acid, hydrolyzed to the hydroxy acid. Starting from MHA hydrolyzate, which also contains appropriate amounts of water and ammonium hydrogen sulfate, there are various isolation methods for the valuable product MHA, which are described in DE-OS 19524054 and in DE Patent 44 28 608 in summary form.

These methods include either solvent extraction or precipitation steps or a combination of both for MHA separation from the salt co-produced. Corresponding MHA-containing solutions are concentrated by evaporation in each of these processes. The production of an amount of up to 27 molar % MHA dimers and MHA oligomers must be accepted therewith.

The only way to keep the undesired oligomer components relatively low and to produce a high concentration of MHA almost free of water with a low amount of oligomers (below 10 molar %) is by means of the protective method of evaporation of an organic MHA extraction solution described in DE-OS 19524054. However, the concentration of oligomers rises after several months of storage to over 50 molar %.

A decrease of the oligomer content in the equilibrium to a maximum of 20 molar % succeeds by dilution with water and additionally mixing with methionine or ammonia, which converts a corresponding amount of the MHA into the MHA ammonium salt. A further decrease of the still-present amount of oligomers, which are less effective from the standpoint of nutrition, in an industrial MHA product thus is still desirable.

Furthermore, the products which can be produced according to DE-OS 19524054 as well as the previously available commercial products have an intense brown color with iodine color indices (IFZ) of 20 to over 300 which can be traced back to the oligomeric component and/or also to impurities which are not specifically known. A colorless product was not able to be industrially produced in the past even though this must be characterized as desirable in the sense of a stable, quality improvement of the product.

Distillation of the raw material, which is a known purification method, is discouraged by the high boiling point of MHA of approximately 170° C. at 3 hPa and by the pronounced tendency to autocatalytic oligomer formation. Experiments in a vacuum distillation apparatus resulted, as expected, on account of the formation of MHA oligomer and polymer products, in a low yield of approximately 0.2% of the theoretical yield of distilled MHA. The main portion remained as a dark-brown and viscous material in the distillation bottom (see also Reference Example 3).

SUMMARY OF THE INVENTION

In view of the documented state of the art, the invention has the purpose of providing a method for producing 2-hydroxy-4-methylthiobutyric acid (MHA) which can be carried out industrially and which results in a decrease of the dimer and oligomer content and in an improvement of color and storage stability.

If the 2-hydroxy-4-methylthiobutyric acid (MHA) exhibiting these improved qualities is characterized by the general quality of stability in storage, such a product is obtained by using a method in which a highly-concentrated liquid MHA containing >95% by weight monomeric and oligomeric components of MHA is distilled under reduced pressure at a temperature at which the monomeric MHA is converted into the gaseous state in a time period which is so short that the formation of significant by-product components is avoided. In particular, short-path evaporators have proved to be suitable for this method, within the framework of the invention. Highly-concentrated MHA solutions of this composition are obtained e.g. according to the method described in DE-OS 19524054. The highly-concentrated MHA produced in this manner or possibly also in some other way is then distilled, preferably at a pressure between $1 \times 10^{-3}$ and $5 \times 10^4$ Pa, especially in a temperature range between 40° and 200° C. The average residence time of the MHA in the distillation is advantageously between 1 and $1 \times 10^4$ seconds.

DETAILED DESCRIPTION OF THE PREFERRED EMBODIMENTS

The distilled MHA obtained from the condenser is almost colorless, partially crystalline at room temperature and surprisingly turns out to be totally free of dimers and higher oligomers. The dark brown bottom product includes hardly any monomeric MHA. It consists mainly of dimers and oligomers in a total amount that increases only insignificantly during the course of the distillation. Thus, the deterioration of the product that is expected according to the state of the art does not occur during distillation according to the invention.

Figure 2:
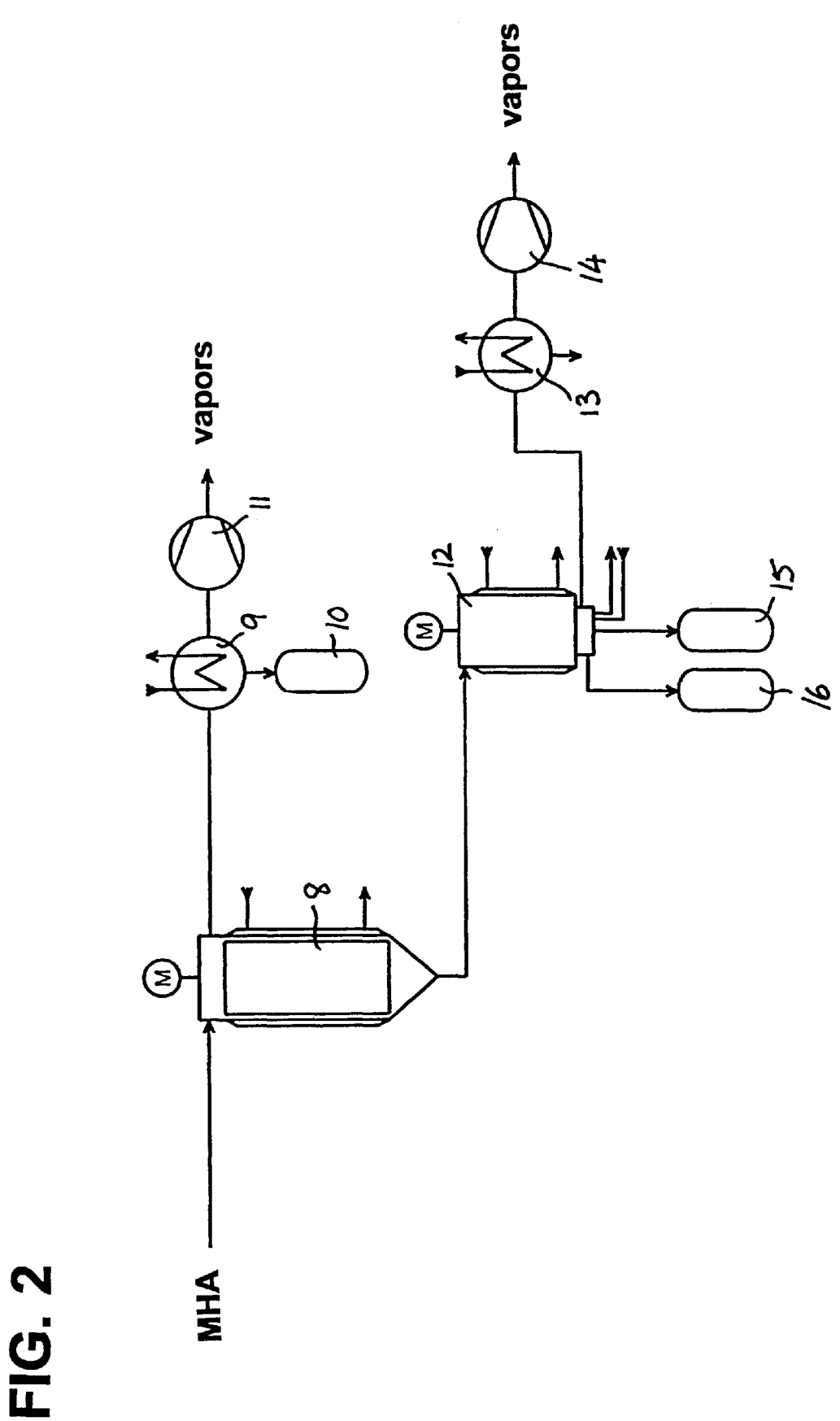
FIG. 2 shows, schematically, apparatus used for the method of Example 2 of the invention.

In addition, it was found that commercial MHA solutions can also be distilled advantageously in accordance with the invention. Aqueous solutions with an 88–90% by weight MHA content are advantageously distilled in a two-stage distillation apparatus, having a film evaporator and a short-path evaporator, as shown in FIG. 2. The water is separated off essentially in the first stage film evaporator The highly-concentrated MHA obtained in the bottom runoff of the first evaporator can be distilled as described above so that essentially only the dimer and oligomer component already present remains as bottom product. On the other hand, the MHA monomer component present is separated off as an oligomer-free distillate with a very pale clear color. The iodine color indices (IFZ) of the distillates of 4 to 5 are much more favorable than the iodine color indices of up to 315 measured for the non-distilled commercial products.

In addition to the superb color properties and the absence of the undesired dimer components and oligomer components (DIM+OLI) in the primary product, the MHA produced in accordance with the invention and the MHA mixed products produced from it surprisingly have a distinctly better stability in storage in comparison to the corresponding products described in DE-OS 19524054.

Figure 3:
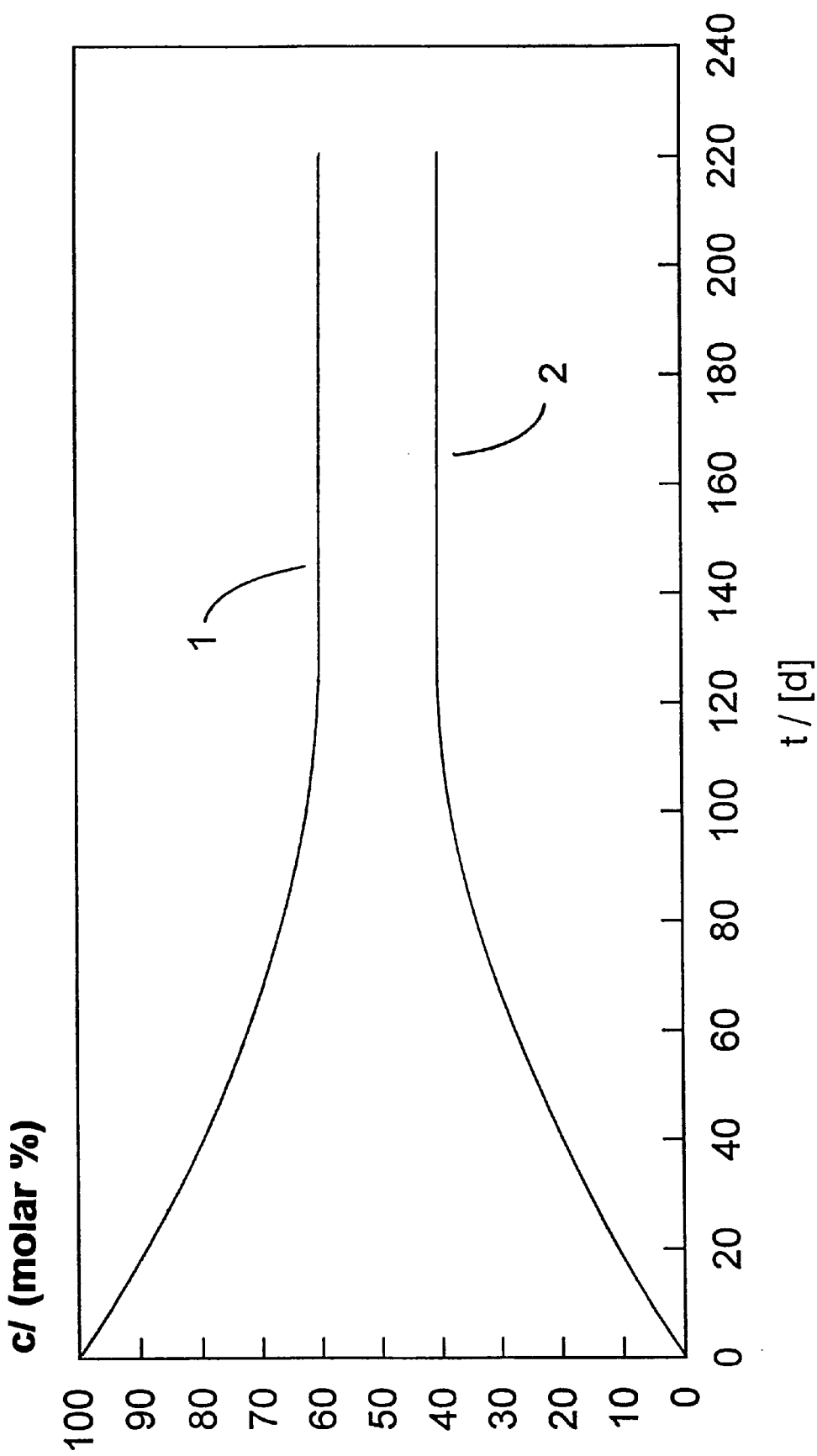
FIG. 3 shows, graphically, concentration of MHA monomers (curve 1) and MHA dimers and oligomers (curve 2), according to time.

This can be recognized in that a highly-concentrated MHA distilled in accordance with the invention has a distinctly lower equilibrium component after approximately 120 days storage with 40 molar % DIM+OLI (FIG. 3) than a non-distilled, highly-concentrated MHA according to DE-OS 19524054 analogously stored with an equilibrium component of approximately 53 molar % DIM+OLI. The adjustment of the equilibrium takes place in a retarded manner in the case of the MHA distilled in accordance with the invention. This extends the availability range of a product with a high monomeric component in a favorable manner.

Figure 4:
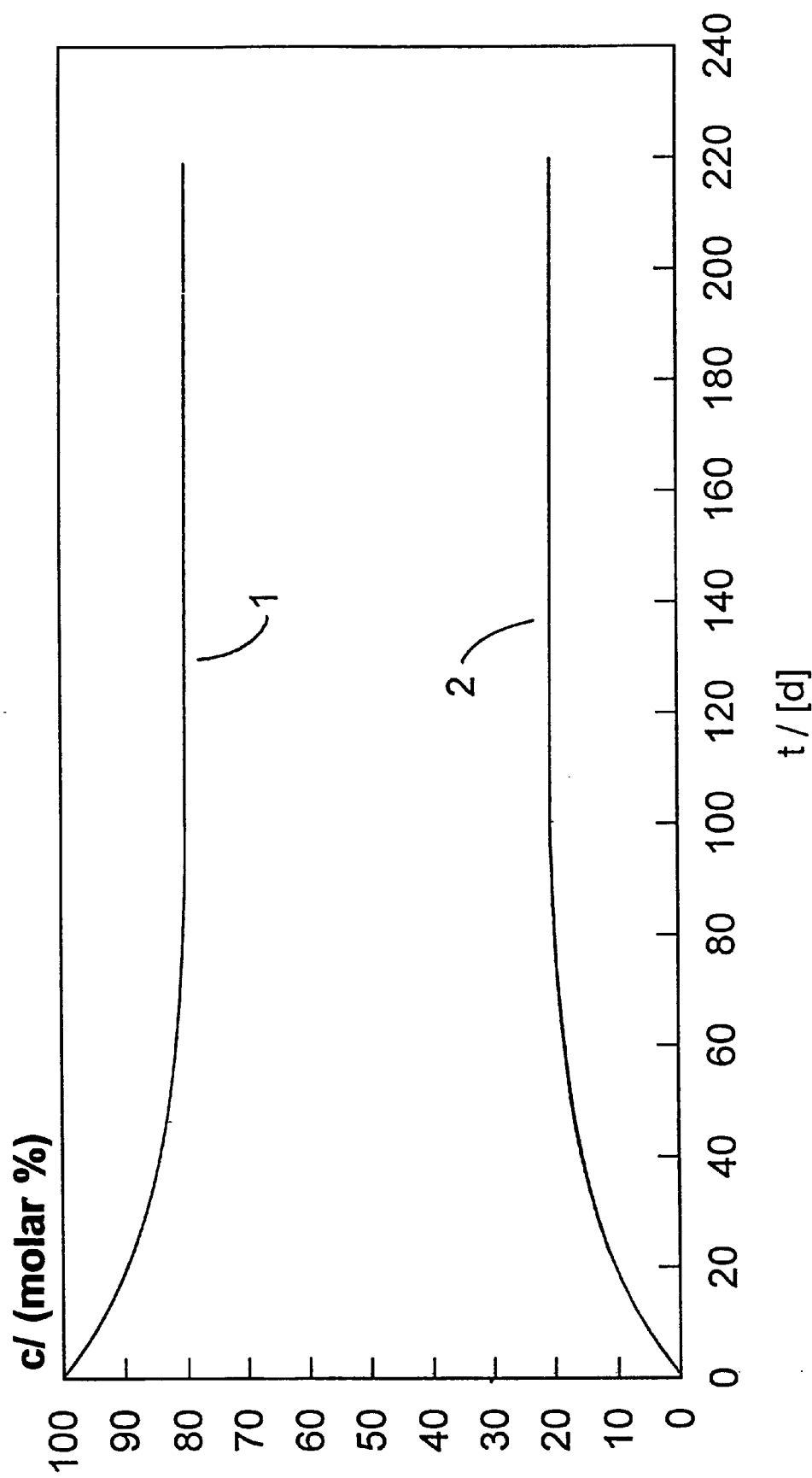
FIG. 4 shows, graphically, concentration of MHA monomers (curve 1) and MHA dimers and oligomers (curve 2) according to time.

A similar favorable effect on the position of equilibrium was surprisingly also able to be determined in a dilution product of distilled MHA and water. The distilled MHA diluted to the commercial concentration of 88% by weight had, after approximately 90 days of storage, an oligomer component in the equilibrium mixture of only 20 molar % DIM+OLI (FIG. 4) in comparison to the commercial product with 26 molar % DIM+OLI according to DE-OS 19524054.

Figure 5:
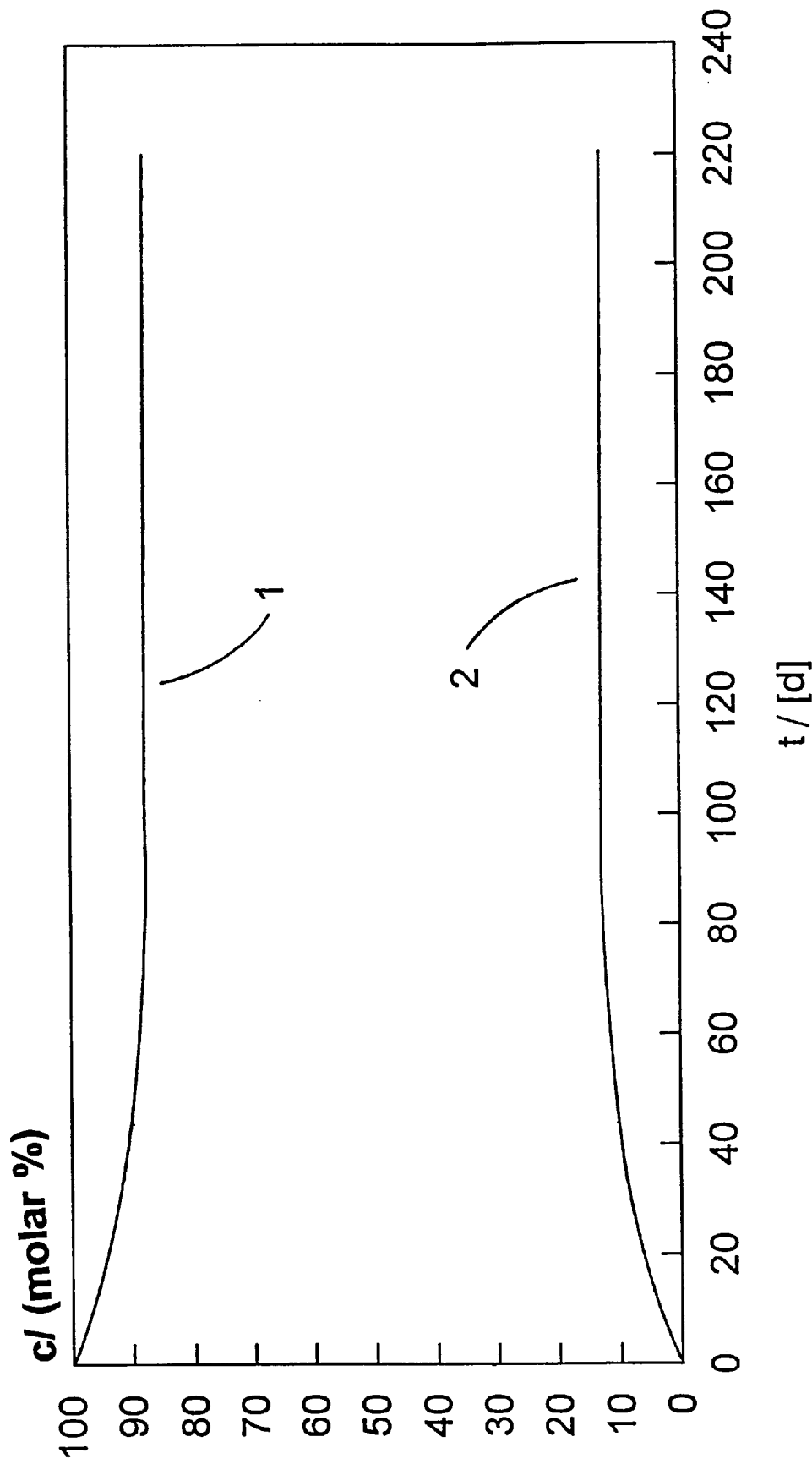
FIG. 5 shows, graphically, concentration of MHA monomers and MET (curve 1) and MHA dimers and oligomers (curve 2) according to time.

A surprisingly even greater reduction of the oligomer content can be observed in the production of a mixed product consisting of MHA and methionine (Met) starting from the distilled MHA produced here. A solution produced in this manner and consisting of 78% MHA+10% Met in water has, with only 13 molar % DIM+OLI in equilibrium after more than 90 days storage (see FIG. 5), an oligomer component that is again distinctly lower in comparison to commercial MHA 88 and in comparison to the MHA 78%+10% Met with 20 molar % DIM+OLI produced according to DE-OS 19524054.

Figure 6:
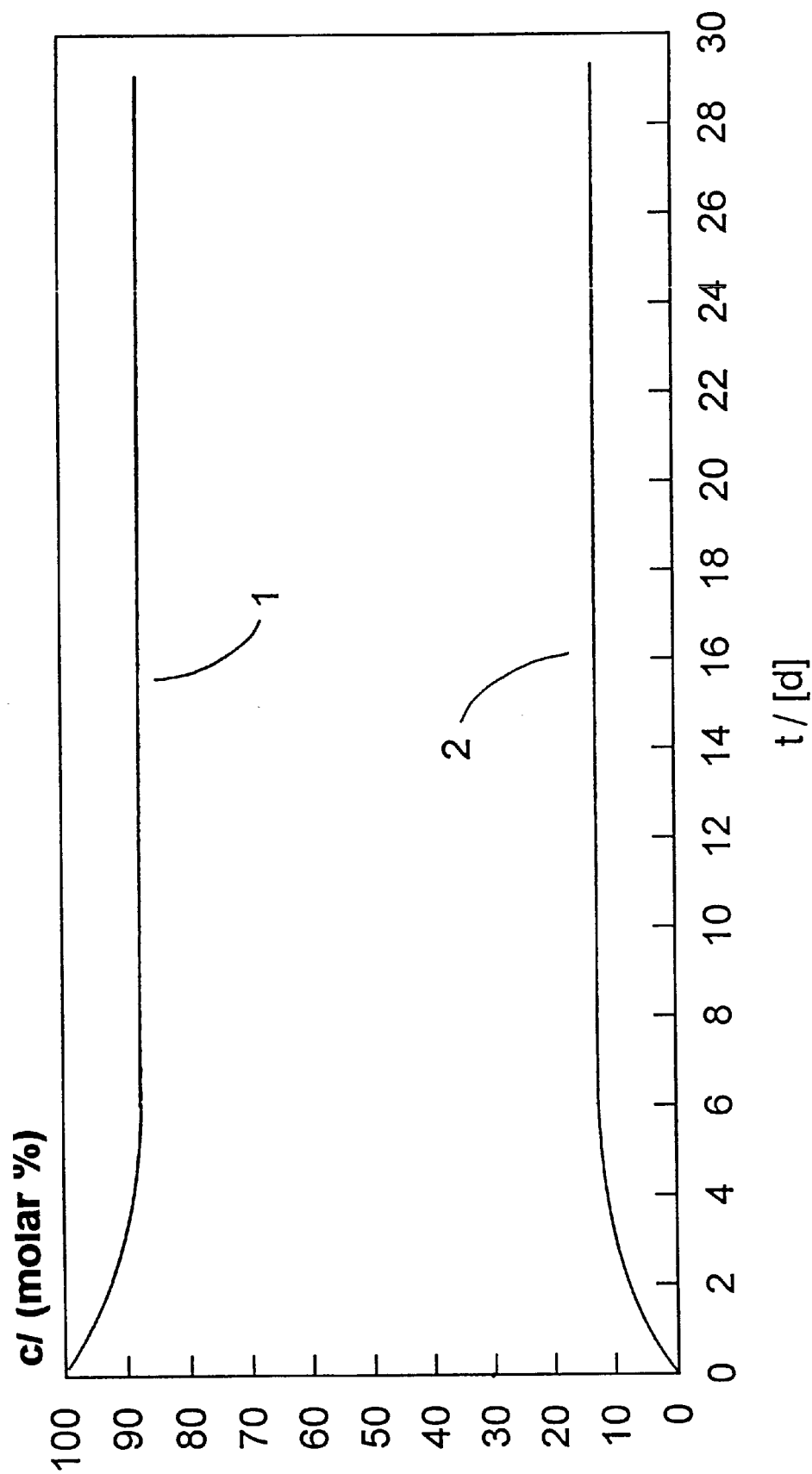
FIG. 6 shows, graphically, concentration of MHA monomers (curve 1) and MHA dimers and oligomers (curve 2) according to time.
Figure 7:
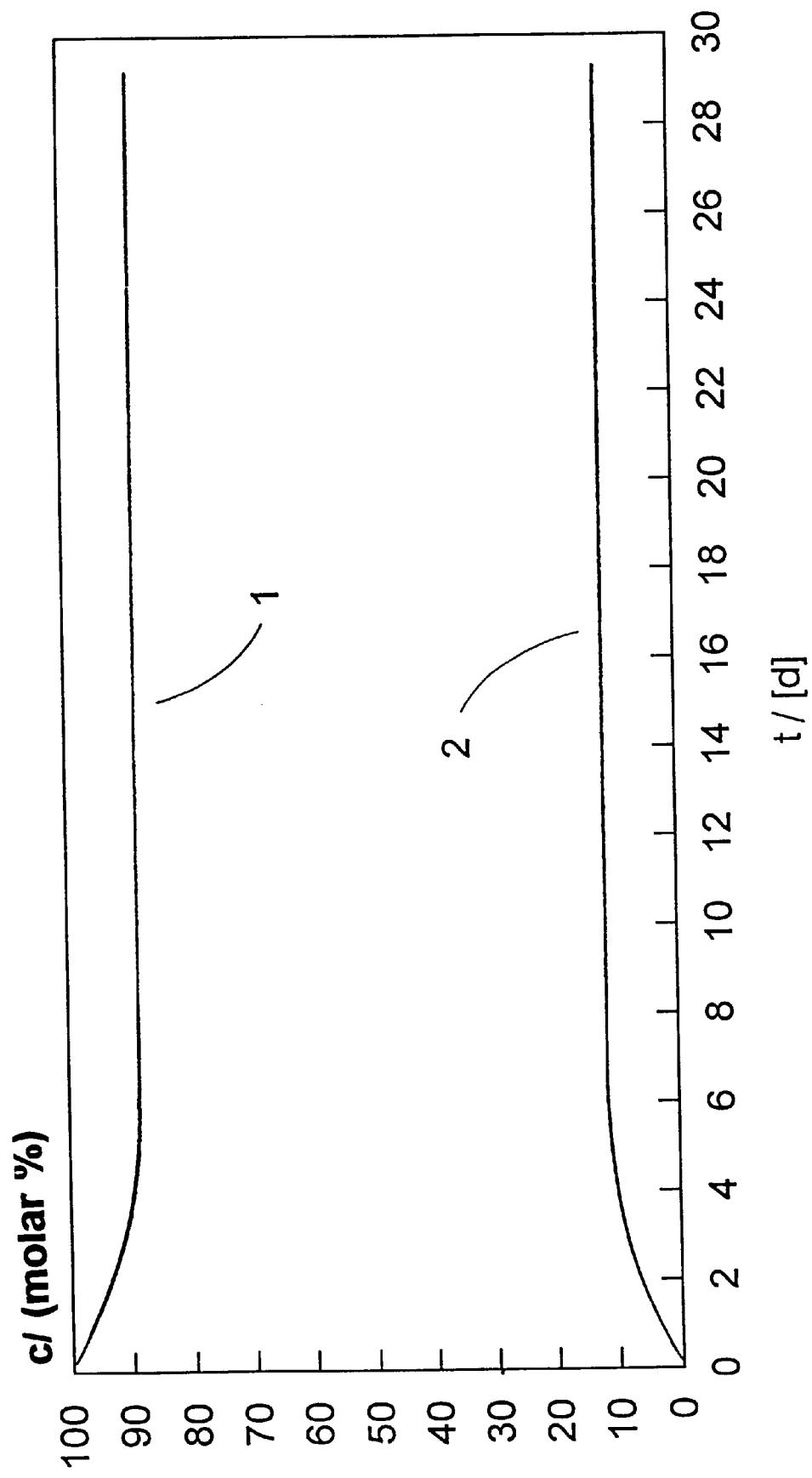
FIG. 7 shows, graphically, concentration of MHA monomers (curve 1) and MHA dimers and oligomers (curve 2) according to time.

The mixtures MHA 78%+10% MHA-$NH_4$ (ammonium salt) and MHA 69%+19% MHA-$NH_4$ containing MHA-$NH_4$ salt (see FIGS. 6 and 7) have, with only 12 and 11 molar % DIM+OLI after 30 days storage at 40° C., even lower values in equilibrium and a distinct improvement compared to the MHA 78%+10% MHA-$NH_4$ mixture with 20 molar % of non-distilled highly-concentrated MHA according to DE-OS 19524054.

In addition, iodine color indices of only 2.5 to 4 are found in MHA 88 as well as in MHA/Met and MHA/MHA-$NH_4$ solutions with 88% by weight active-substance content, which indices are far more favorable than in the previously available commodity.

All the products named here remain clear liquids with almost unchanged color values even after more than 230 days of storage.

Figure 8:
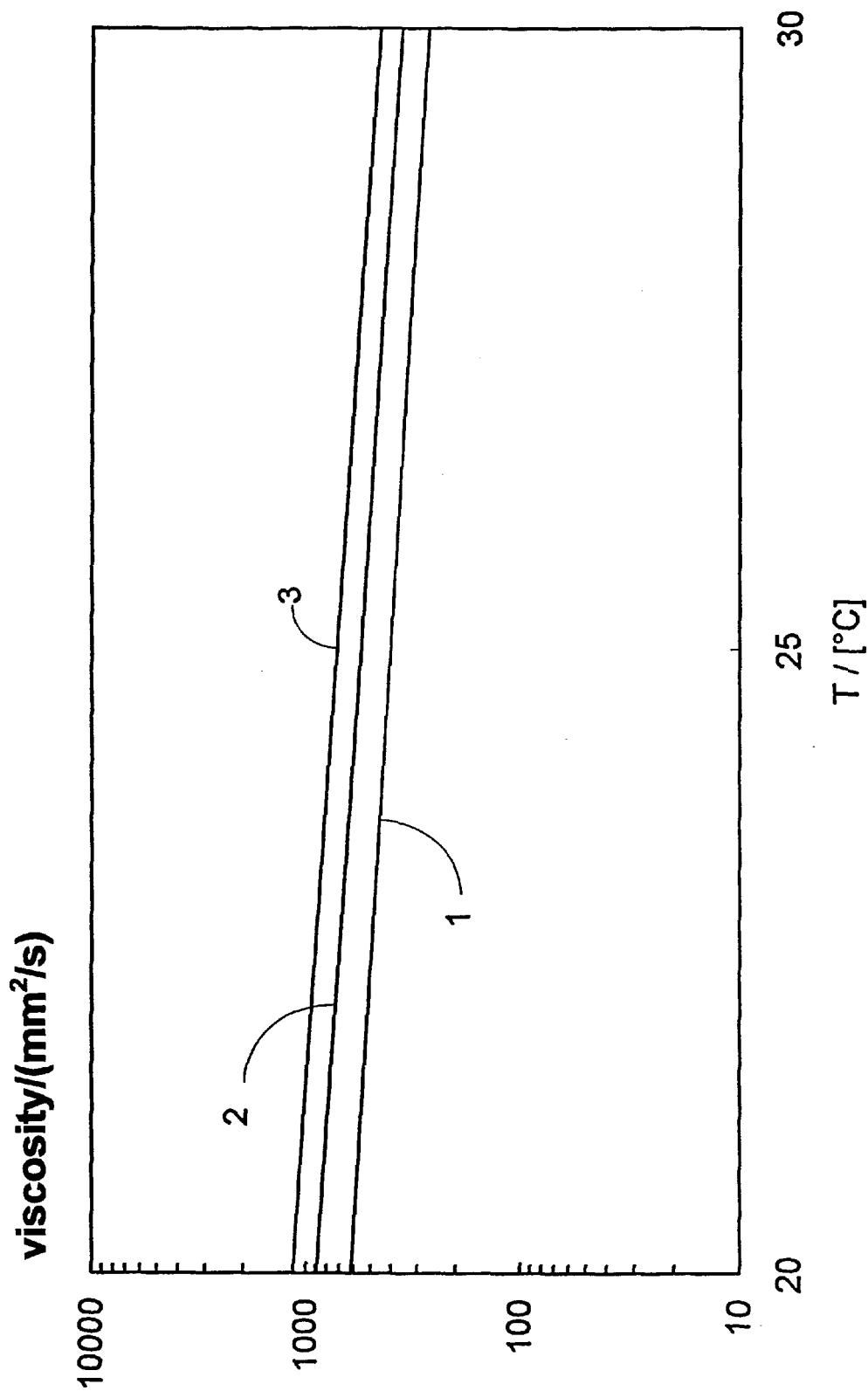
FIG. 8 shows, graphically, viscosity measurements according to temperature for MHA distillate produced according to Example 4.
Figure 9:
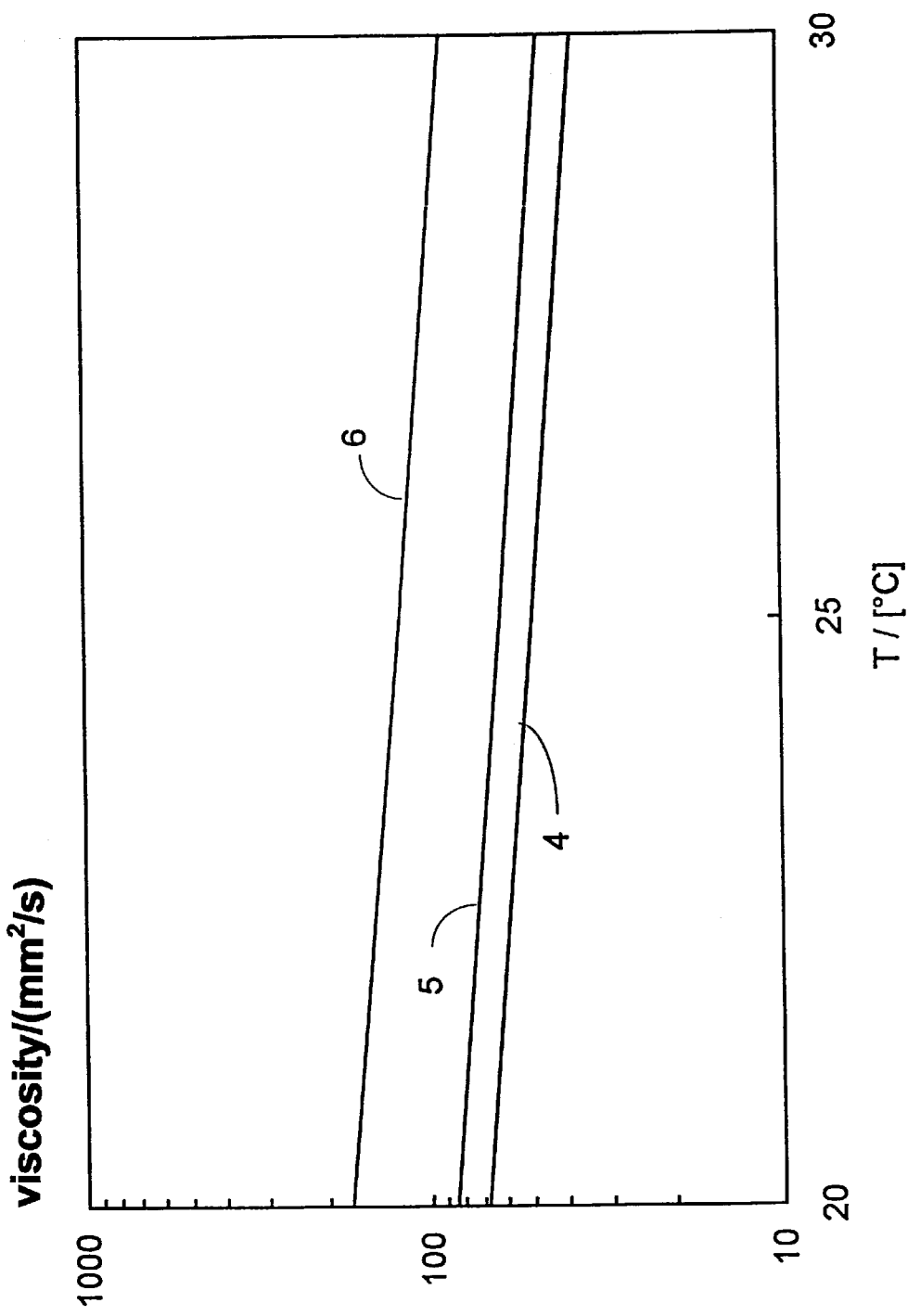
FIG. 9 shows, graphically, viscosity measurements according to temperature for MHA 88 produced according to Example 4 in comparison with commercially available MHA 88.
Figure 10:
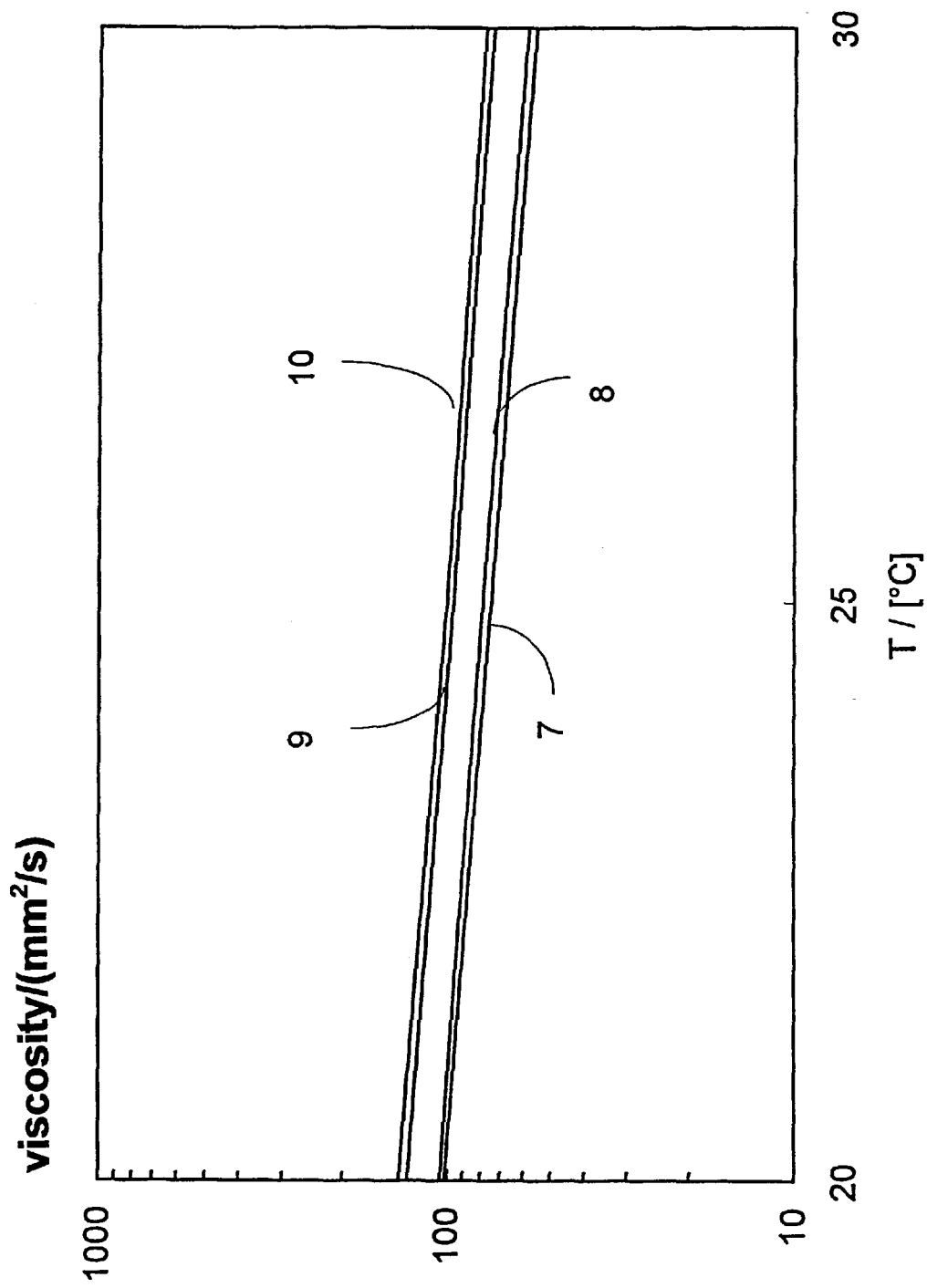
FIG. 10 shows, graphically, viscosity measurements according to temperature for MHA and MHA-$NH_4$ produced according to Example 4.
Figure 11:
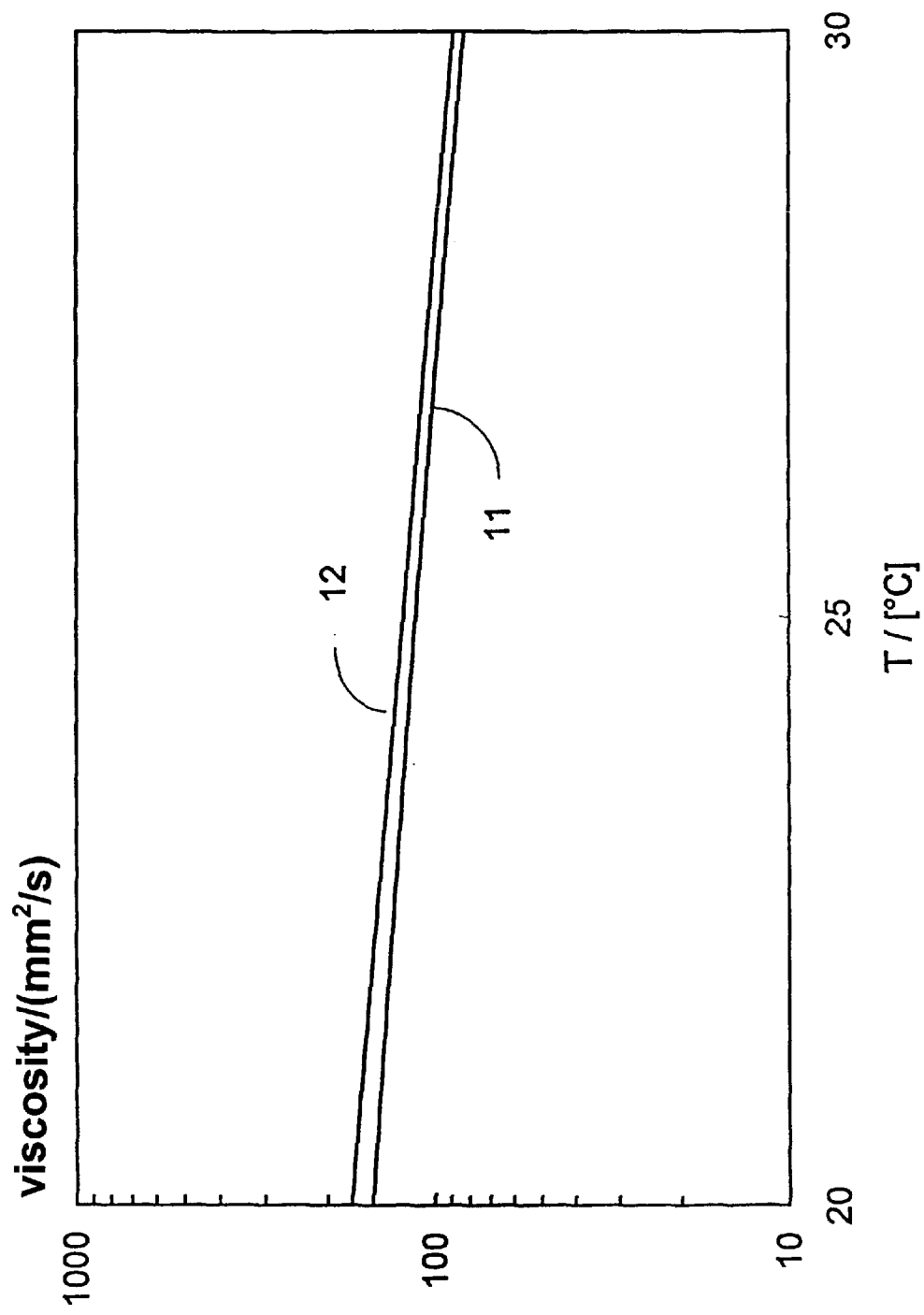
FIG. 11 shows, graphically, viscosity measurements according to temperature for mixtures of MHA and Met produced according to Example 4.

The viscosity properties of MHA formulations are as a rule advantageously influenced by the preceding distillation stage (see FIGS. 8–11). Thus, a viscosity value clearly below the viscosity range of the available commercial products of 61 to 122 $mm^2$/s was found for MHA 88 from distilled MHA with 50 $mm^2$/s (FIG. 9). MHA/Met as well as MHA/MHA-$NH_4$ mixtures are in the same viscosity range, given otherwise improved properties (FIGS. 10 and 11). Stored MHA distillate has, with 402 $mm^2$/s (FIG. 8), a viscosity value below stored non-distilled highly-concentrated MHA of 517 $mm^2$/s in accordance with DE-OS 19524054.

Advantages of the Method of the Invention

The lower oligomer component of stored distilled MHA is an extraordinary advantage because the viscosity is reduced and thus the handling properties are improved as well as improving the ability to pump and transport the MHA.

Even more significant is the distinct improvement of the biological quality due to the amount, which is significantly higher in the equilibrium mixture, of monomeric MHA in MHA 88 and in MHA/MHA-NH$_4$ mixtures as well as of monomeric MHA+methionine in MHA 78%+10% Met, in comparison to the previously available products. The oligomer component can even be held substantially below 10 molar % if the product is used within only a few days, which results in a further increase of the biological quality.

Further advantages are the greater purity and the distinctly clearer color, which result in greater product acceptance by the producers of high-grade fodder.

In addition thereto, the highly-concentrated MHA distilled in accordance with the invention is very well suited for the production of D,L-MHA pharmaceutical goods and corresponding pharmaceutical formulations such as the initially cited MHA calcium salt for the treatment of renal insufficiency. In this instance the previously customary purification process, which included several stages such as oligomer splitting, extraction and purification of the calcium salt by expensive crystallization, can be eliminated. A simple neutralization of the MHA distillate in accordance with the invention with a suitable calcium base, such as e.g. calcium hydroxide, and the subsequent drying is sufficient in this instance to achieve the required product quality.

The distillation in accordance with the invention in combination with a short residence time in e.g. a short-path evaporator makes it possible to make available a high-purity MHA and, at the same time, an improved MHA product distinguished by greater purity and greater storage stability as well as by greater biological quality when used as fodder additive.

Figure 12:
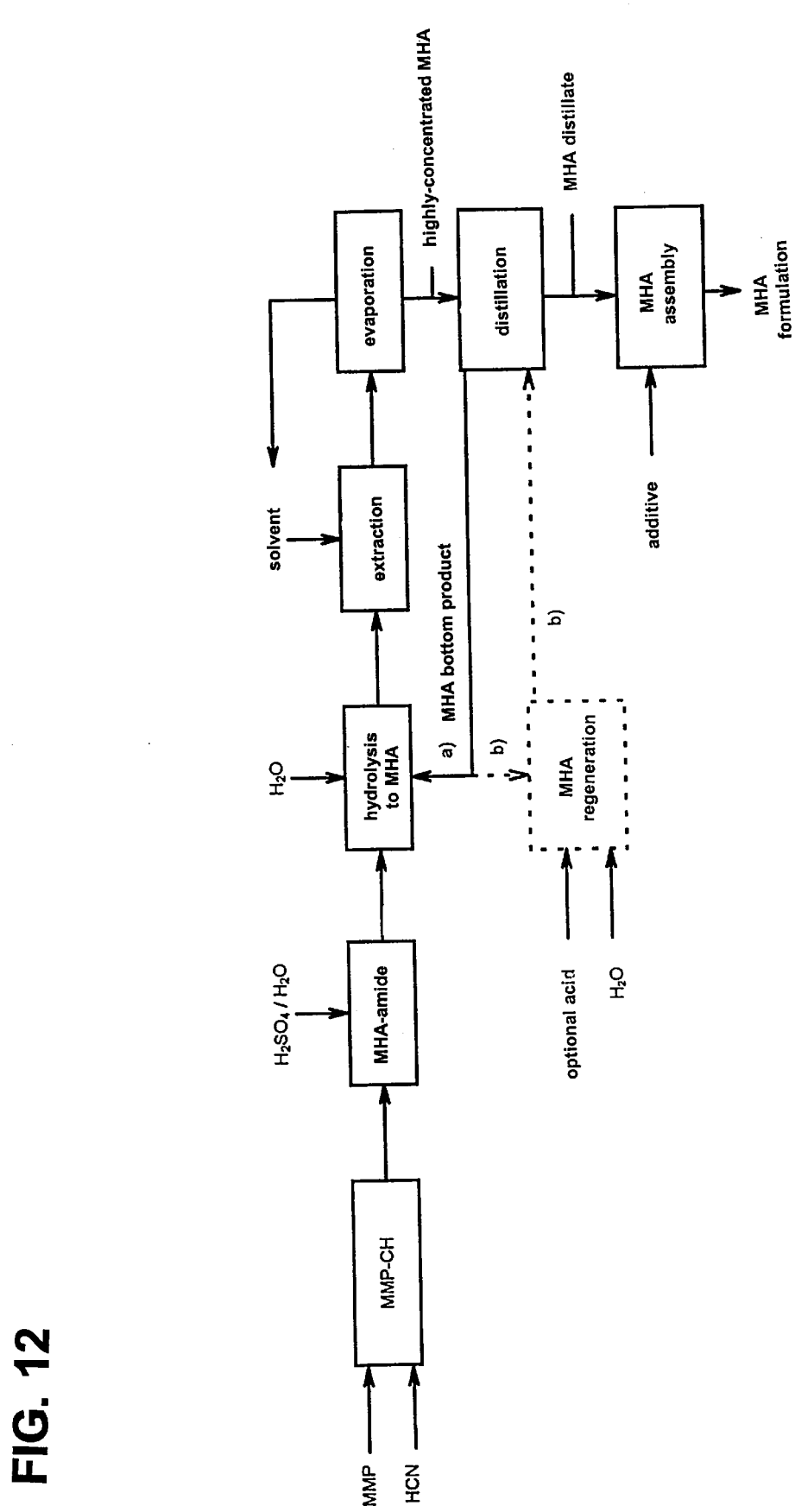
FIG. 12 shows, schematically, apparatus for practicing the method of the invention.

The combination of the distillation of the invention with a method of producing MHA described in DE-OS 19524054 is especially advantageous. The MHA formulations which are stable in storage are directly produced thereby in a corresponding total method as is shown in FIG. 12 starting from 3-methylmercaptopropionaldehyde (MMP) and hydrogen cyanide (HCN).

In addition, the high-purity method found here can also be used with the currently commercially available 88–90% MHA solutions and basically also with any other MHA-containing solution in order to produce the corresponding improved MHA from them.

According to the invention the bottom products accumulating during the distillation and consisting primarily of undesired MHA dimers and oligomers do not have to be discarded. Rather, there is the possibility of converting these MHA dimers and oligomers, hydrolytically by a simple dilution with water, to a suitable concentration of 10 to 90% by weight and optionally, with the addition of suitable amounts of acid, especially of sulfuric acid, and by simply heating them hydrolytically to a temperature of 50 to 140° C., into the MHA monomer and then purifying the MEA monomer by distillation.

Such MHA regeneration and recycling can be realized in an especially elegant manner in an appropriate re-circulation process in which the bottom product of the distillation is continuously supplied to an appropriate ester hydrolysis stage and the MHA ester hydrolyzate, rich in MHA monomers, is subsequently returned into the distillation stage. In this instance too the combination with an MHA process, such as the one described in DE-OS 19524054, is especially advantageous since the bottom product can be returned into the stage of the sulfuric-acid hydrolysis of MHA amide which must be carried out (see path a) in FIG. 12). The MHA ester component, which as a rule does not comprise more than 25 molar % and is to be hydrolyzed in addition, can be reduced without problems, as shown by tests 1 and 2 in Example 7, within this stage to the customary dimer and oligomer component of approximately 5 to 15 molar %. It is possible to add the distillation bottom before the beginning of the hydrolysis stage or at any later time desired during the reaction to the MHA hydrolyzate already formed up to that point. The amide hydrolysis stage is only insignificantly loaded thereby and an additional hydrolysis stage can be eliminated. The amount of regenerated MHA from the distillation bottom is supplied together with the product stream via extraction and evaporation back to the distillation stage.

However, it is just as possible to hydrolyze the dimeric and oligomeric MHA ester acids in an additional step (see path b) in FIG. 12). In order to accelerate the reaction, which can also be carried out autocatalytically, it is especially advantageous in this instance to add small amounts of acid, especially mineral acids such as HCl or $H_3PO_4$, but preferably $H_2SO_4$, as is made clear in Example 7, Test 3. The use of acidic ion exchangers is also possible in this connection, as Test 4 in Example 7 shows, in which instance the advantage resides in the fact that no additional acid is entrained into the distillation stage. The last-named variant is mainly to be used if a start is to be made from commercial MHA product. The MHA distillation and the recovery of monomeric MHA from the MHA bottom product can thus also be a component of the total MHA method shown in FIG. 12 for producing high-purity MHA formulations which are stable in storage.

Both an MHA distillation method with MHA bottom-product regeneration and the previously cited total method operate practically without MHA losses even though a highly purified monomeric MHA is produced as final product. This represents a special advantage, particularly from the viewpoints of economy and modern ecology.

The following preparative examples clarify the subject matter of the invention further:

Analytic Determination Methods and Definitions

The contents of MHA monomer and methionine were quantitatively determined in the process solutions by HPLC by means of a comparison with an external standard (pure substance). No distinction can be made analytically thereby between the monomer as free acid and the optional monomeric component also present as MHA-NH$_4$ salt. The MHA-NH$_4$ component is calculated in this instance from the NH$_4$ content.

The content of MHA total=MHA monomer+MHA (dimers+oligomers)+methionine (optional)+MHA-NH$_4$ (optional) was determined by titrimetric determination of the thioether function with KBr/KBrO$_3$ standard solution and expressed as the sum of the corresponding MHA monomer equivalents in (% by weight) and (g) and (mol) and (molar %).

The content of MHA dimers+MHA oligomers (DIM+OLI) was determined by calculating the difference of MHA total and MHA monomer (+optional methionine) and expressed as a sum of the corresponding MHA monomer equivalents in (% by weight) and (g) and (mol) and (molar %).

The water content was determined by titration according to Karl-Fischer, and the sulfate content and ammonium content were determined by ion chromatography according to standard methods.

The iodine color index (IFZ) was determined according to DIN 6162.

EXAMPLE 1

Figure 1:
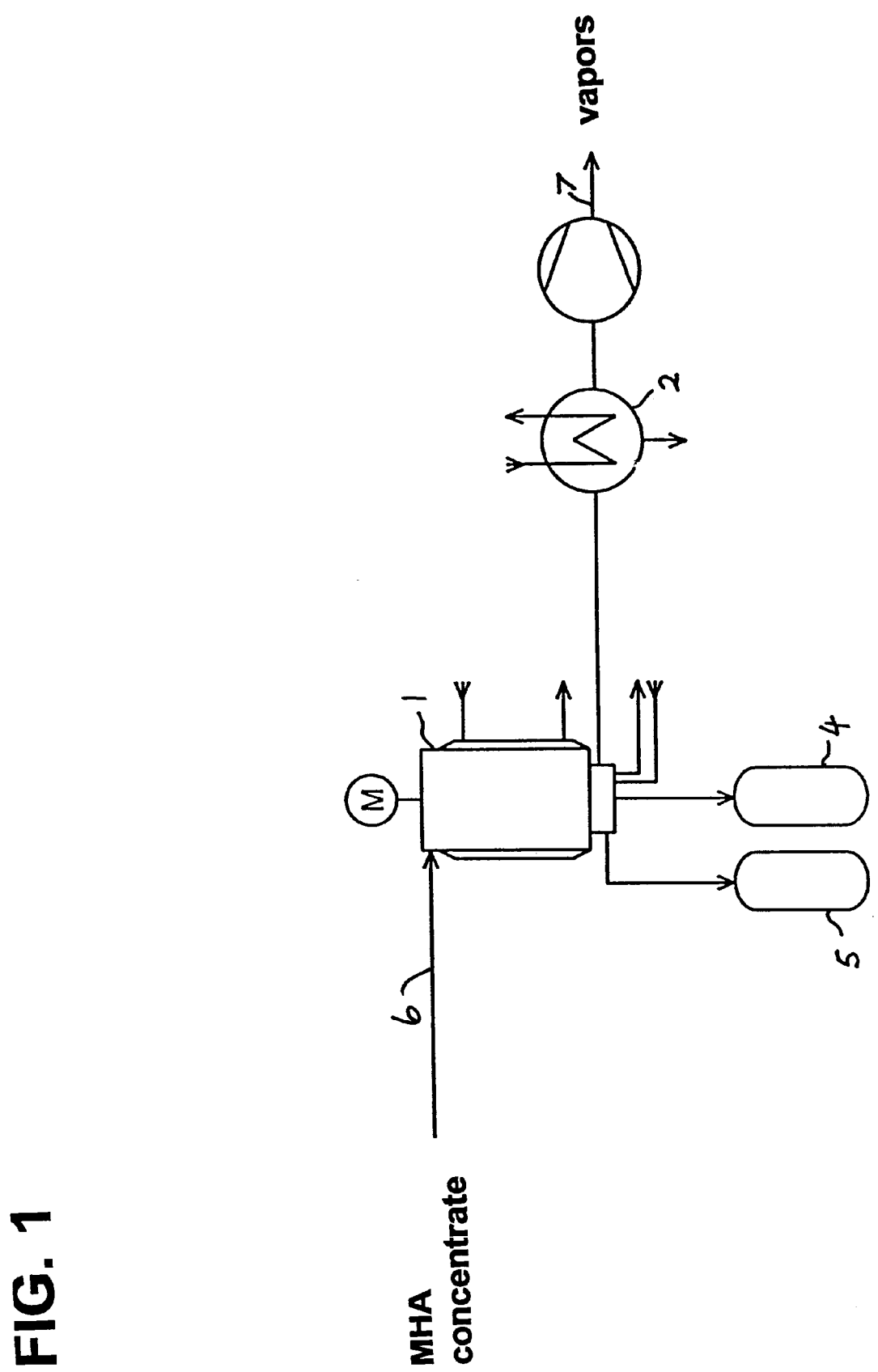
FIG. 1 shows, schematically, apparatus used for the method of Example 1 of the invention.

FIG. 1 shows, schematically the apparatus used for Example 1, having the following arrangement:

An industrial metallic short-path evaporator 1 with 0.35 m² exchange surface, heated double jacket and tempered condensation surface is provided with a container 4 for receiving distillation product and a container 5 for receiving bottom product. Condenser 2 of vacuum system 3 for producing a high vacuum are also part of the evaporator system. MHA concentrate is fed into evaporator 1 through pipe 6 and any vapors are collected from exit pipe 7.

8.9 kg/h highly-concentrated MHA was fed from an evaporation system for obtaining highly-concentrated MHA from an MIBK-MHA extract solution (analogously to DE-OS 19524054) into short-path evaporator 1 through pipe 6. 7.4 kg/h MHA distillate was obtained in container 4 and 1.4 kg/h bottom product was obtained in container 5. The test parameters are set forth in the following table:

Infeed into short-path evaporator 1:
Inflow rate of highly-concentrated MHA: 8.9 kg/h
Composition of highly-concentrated MHA:

| | | |
|---|---|---|
| MHA total | 99.6% by weight | 100 molar % |
| MHA monomer | 84.6% by weight | 84.9 molar % |
| MHA DIM + OLI | 15.0% by weight | 15.1 molar % |
| $H_2O$ | 0.2% by weight | |
| $SO_4$ | 0.2% by weight. | |
| Evaporation Pressure: | 0.1 hPa in evaporator 1 | |
| Temperatures: | In the inflow stream | 60° C. |
| | In the heating jacket | 125° C. |
| | In the condenser | 45° C. |
| | In the bottom runoff | 108° C. |

Product amounts:

<0.1 kg/h in the cooling trap 2
1.4 kg/h in the bottom runoff with 99.8% by weight MHA total
7.4 kg/h MHA distillate in product container 4 with the following composition:

| | | |
|---|---|---|
| MHA total | 99.9% by weight | 100 molar % |
| MHA monomer | 99.9% by weight | 100 molar % |
| MHA DIM + OLI | 0% by weight | 0 molar % |
| $H_2O$ | <0.1% by weight | |
| $SO_4^{2-}$ | 0% by weight | |

EXAMPLE 2

FIG. 2 shows, schematically, the apparatus used for Example 2.

MHA 88 commercial product (Alimet™ or Rhodimet AT88™) was fed continuously into film evaporator 8 having 0.06 m² exchange surface, which was provided with a water coated glass condenser 9. Water obtained during the evaporation was collected in container 10. The bottom runoff product was continuously supplied to short-path evaporator 12, having 0.05 m² exchange surface. MHA distillate evaporated therein was collected in product container 15. Bottom product containing MHA dimers and—oligomers was collected in bottom product container 16.

Test 1

Infeed into film evaporator 8:
Inflow rate Alimet ™ (NOVUS): 0.196 kg/h
Composition:

| | | |
|---|---|---|
| MHA total | 88.6% by weight | 100 molar % |
| MHA monomer | 67.7% by weight | 76.4 molar % |
| MHA DIM + OLI | 20.9% by weight | 23.6 molar % |
| $H_2O$ | 11.4% by weight | |
| $SO_4^{2-}$ | 0.9% by weight | |
| IFZ | 24 | |
| Evaporation Pressure: | 24 hPa in evaporator 8 | |
| Temperatures: | In the inflow stream | 29° C. |
| | In the heating jacket | 140° C. |
| | Vapors | 50° C. |
| Evaporation Pressure: | 0.2 hPa in evaporator 12 | |
| Temperatures: | In the inflow stream | ~120° C. |
| | In the heating jacket | 155° C. |
| | In the condenser | 40° C. |

Product amounts:

0.035 kg/h condensate in container 10
0 kg/h condensate in condenser 13
0.113 kg/h MHA distillate in product container 15 has the following composition:

| | | |
|---|---|---|
| MHA total | 100% by weight | 100 molar % |
| MHA monomer | 100% by weight | 100 molar % |
| MHA DIM + OLI | 0% by weight | 0 molar % |
| $H_2O$ | 0% by weight | |
| $SO_4^{2-}$ | 0% by weight | |
| IFZ | 5 | |

0.038 kg/h bottom product in container 16 has the following composition:

| | | |
|---|---|---|
| MHA total | 100% by weight | 100 molar % |
| MHA monomer | 14.0% by weight | 14.0 molar % |
| MHA DIM + OLI | 86.0% by weight | 86.0 molar % |
| $H_2O$ | 0% by weight | |
| $SO_4^{2-}$ | 4.6% by weight | |

Test 2

Infeed into film evaporator 8:
Inflow rate Alimet ™ (NOVUS): 0.24 kg/h
Composition:

| | | |
|---|---|---|
| MHA total | 88.6% by weight | 100 molar % |
| MHA monomer | 67.7% by weight | 76.4 molar % |
| MHA DIM + OLI | 20.9% by weight | 23.6 molar % |
| $H_2O$ | 11.4% by weight | |
| $SO_4^{2-}$ | 0.9% by weight | |
| IFZ | 24 | |
| Evaporation Pressure: | 24 hPa in evaporator 8 | |
| Temperatures: | In the inflow stream | 26° C. |
| | In the heating jacket | 140° C. |
| | Vapors | 47° C. |
| Evaporation Pressure: | 0.2 hPa in evaporator 12 | |
| Temperatures: | In the inflow stream | ~120° C. |
| | In the heating jacket | 155° C. |
| | In the condenser | 40° C. |

Product amounts:

0.042 kg/h condensate in container 10
0 kg/h condensate in condenser 13
0.129 kg/h MHA distillate in product container 15 with the following composition:

| | | |
|---|---|---|
| MHA total | 99.9% by weight | 100 molar % |
| MHA monomer | 99.4% by weight | 99.5 molar % |
| MHA DIM + OLI | 0.5% by weight | 0.5 molar % |
| $H_2O$ | <0.1% by weight | |
| $SO_4^{2-}$ | 0% by weight | |
| IFZ | 5 | |

0.050 kg/h bottom product in container 16 with the following composition:

| | | |
|---|---|---|
| MHA total | 100% by weight | 100 molar % |
| MHA monomer | 8.0% by weight | 8.0 molar % |
| MHA DIM + OLI | 92.0% by weight | 92.0 molar % |
| $H_2O$ | 0% by weight | |
| $SO_4^{2-}$ | 4.3% by weight | |

Test 3

Infeed into film evaporator 8:
Inflow rate Rhodimet AT88 ™ (Rhone Poulenc): 0.123 kg/h
Composition:

| | | |
|---|---|---|
| MHA total | 89.0% by weight | 100 molar % |
| MHA monomer | 67.5% by weight | 75.8 molar % |
| MHA DIM + OLI | 21.5% by weight | 24.2 molar % |
| $H_2O$ | 10.6% by weight | |
| $SO_4^{2-}$ | 1.39% by weight | |
| IFZ | 315 | |
| Evaporation Pressure: | 24 hPa in evaporator 8 | |

-continued

| Temperatures: | In the inflow stream | 28° C. |
| | In the heating jacket | 140° C. |
| | Vapors | 44° C. |
| Evaporation Pressure: | 0.4 hPa in evaporator 12 | |
| Temperatures: | In the inflow stream | ~120° C. |
| | In the heating jacket | 155° C. |
| | In the condenser | 40° C. |

Product amounts:

0.013 kg/h condensate in container 10
0 kg/h condensate in cooling trap 13
0.057 kg/h MHA distillate in product container 15 with the following composition:

| MHA total | 100% by weight | 100 molar % |
| MHA monomer | 100% by weight | 100 molar % |
| MHA DIM + OLI | 0% by weight | 0 molar % |
| $H_2O$ | 0% by weight | |
| $SO_4^{2-}$ | 0% by weight | |
| IFZ | 3.5 | |

0.035 kg/h bottom product in container 16 with the following composition:

| MHA total | 100% by weight | 100 molar % |
| MHA monomer | 42.0% by weight | 42.0 molar % |
| MHA DIM + OLI | 58.0% by weight | 58.0 molar % |
| $H_2O$ | 0% by weight | |
| $SO_4^{2-}$ | 4.8% by weight | |

EXAMPLE 3

Reference Example: Distillation according to the state of the art
Yield MHA distillate: 0.2% of theory 800 g MHA hydrolyzate (37.4% by weight MHA total, with 10.7 molar % DIM+OLI) produced analogously to the method of DE-OS 19524054, Example 3, was extracted in a separating funnel with 480 g methylisobutylketone and the extraction solution was washed with 50 g water. The extraction solution was evaporated on a rotary evaporator in a water-jet vacuum. The oily evaporation residue consisting of 91.2% by weight MHA total with 81.9 molar % MHA monomers and 18.1 molar % MHA DIM-OLI was distilled in a fractionating procedure via a distillation bridge in an oil pump vacuum:

Pressure: 0.2 hPa
Temperatures: In the bottom: 150° C.
  Vapors: approximately 55° C.
  Condenser: 40° C.

The following was obtained after 2 hours:
0.5 g MHA distillate in the receiving flask with the following composition:

| MHA total | 97.9% by weight | 100 molar % |
| MHA monomer | 86.8% by weight | 88.6 molar % |
| MHA DIM+OLI | <0.1% by weight | <0.1 molar % |

Unknown byproduct approximately 11.1% by weight
246 g bottom product in the distillation flask with the following composition:

| MHA total | 100% by weight | 100 molar % |
| MHA monomer | 8.7% by weight | 8.7 molar % |
| MHA DIM + OLI | 92.3% by weight | 92.3 molar % |

EXAMPLE 4

Production of MHA Formulations

Test 1
MHA distillate
MHA distillate with a content of 99.9% by weight MHA total was produced similarly to Example 1.

Test 2
MHA 88
88.0 g (0.59 mol) fresh MHA distillate from Example 1 was diluted in a beaker equipped with a magnetic stirrer under agitation with 12.0 g water to a MHA total concentration of 88.0 % by weight.

Test 3
MHA 78+10 Met
78.0 g (0.52 mol) MHA distillate which had been freshly produced according to Example 1 was mixed in a beaker, with magnetic stirring under agitation, with 10.0 g (0.067 mol) >99% D,L-methionine and 12.0 g water and a homogeneous solution was produced thereby with the following composition: 88.0% by weight MHA total=78.0% by weight MHA monomer+10.0% by weight methionine 12.0% by weight water.

Test 4
MHA distillate
MHA distillate with a content of 100% by weight MRA total was produced according to Example 2, Test 1.

Test 5
MHA 88
44.0 g (0.29 mol) 100% MHA distillate which had been freshly produced according to Example 2, Test 1 was diluted in a beaker equipped with a magnetic stirrer with 6.0 g water to a concentration of 88.0% by weight MHA total: IFZ 4.

Test 6
MHA 78+10 Met
39.0 g (0.26 mol) 100% MHA distillate which had been freshly produced according to Example 2, Test 1 was mixed in a beaker equipped with a magnetic stirrer under agitation with 5.0 g (0.034 mol) >99% D,L-methionine and 6.0 g water and a homogeneous solution was produced thereby, with the following composition: 88.0% by weight MHA total=78.0% by weight MHA monomer+10.0% by weight methionine 12.0% by weight water IFZ 2.5

Test 7
MHA 78+10 MHA-$NH_4$
60.0 g (0.40 mol) MHA distillate which had been freshly produced according to Example 2, Test 1, was mixed in a beaker equipped with a magnetic stirrer under agitation with 2.26 g (0.040 mol) 30.5% ammonia solution and 6.71 g water and a homogeneous solution was produced thereby, with the following analytic composition:

| MHA total | 87.0% by weight |
| $NH_4^+$ corresponding to | 1.08% by weight |
| MHA monomer | 78.0% by weight (calc.) + |
| MHA-$NH_4$ | 10.0% by weight (calc.) |
| Water | approximately 12.0% by weight (calc.) |
| IFZ | 2.5 |

Test 8
MA 69+19 MHA-$NH_4$
60.0 g (0.40 mol) MHA distillate which had been freshly produced according to Example 2, Test 1 was mixed in a beaker equipped with a magnetic stirrer under agitation with 4.58 g (0.082 mol) 30.5% ammonia solution and 5.19 g water and a homogeneous solution was produced thereby, with the following composition:

| | |
|---|---|
| MHA total | 86.0% by weight |
| NH$_4^+$ corresponding to | 2.0% by weight |
| MHA monomer | 69.26% by weight (calc.) + |
| MHA-NH$_4$ | 18.63% by weight (calc.) |
| Water | 12.0% by weight (calc.) |
| IFZ | 2.0 |

Test 9

MHA distillate

MHA distillate with a content of 100% by weight MHA total was produced analogously with Example 2, Test 3.

EXAMPLE 5

Storage of MHA Formulations

The products used in FIGS. 3 to 7 were each stored in a closed glass container without agitation at the temperatures indicated there for a period of up to over 230 days. Specimens were taken at regular intervals and the content of MHA total, MHA monomers, MHA (dimers+oligomers) as well as optionally Met determined (see the methods indicated above).

FIG. 3

MHA distillate which was produced according to Example 4, Test 1, has after approximately 120 days of storage at 25° C. an adjusted equilibrium of 60 molar % MHA monomers (curve 1), 40 molar % MHA (dimers+oligomers) (curve 2).

FIG. 4

MHA 88 which was produced according to Example 4, Test 2, has after approximately 90 days of storage at 40° C. an adjusted equilibrium of 80 molar % MHA monomers (curve 1), 20 molar % MHA (dimers+oligomers) (curve 2).

This ratio is clearly below that of commercial product.

FIG. 5

MHA 78+10 Met which was produced according to Example 4, Test 3 has after approximately 90 days of storage at 25° C. an adjusted equilibrium of 87 molar % MHA monomers+Met (curve 1), 13 molar % MHA (dimers+oligomers) (curve 2).

FIG. 6

MHA 78+10 MHA-NH$_4$ which was produced according to Example 4, Test 7, has after approximately 6 days of storage at 40° C. an adjusted equilibrium of 88 molar % MHA monomers (curve 1), 12 molar % MHA (dimers+oligomers) (curve 2).

FIG. 7

MHA 69+19 MHA-NH$_4$ which was produced according to Example 4, Test 8, has after approximately 6 days of storage at 40° C. an adjusted equilibrium of 89 molar % MHA monomers (curve 1), 11 molar % MHA (dimers+oligomers) (curve 2).

A comparison of FIGS. 3 to 7 shows a decrease of the equilibrium components of undesired MHA (dimers+oligomers) components in the MHA formulations in the series MHA distillate, MHA 88, MHA 78+10 Met, MHA 78+10 MHA-NH$_4$, MHA 69+19 MHA-NH$_4$. All MHA formulations cited here have more favorable MHA (dimers+oligomers) components than the corresponding formulations in DE-OS 19524054. All 88% formulations have much more favorable MHA (dimers+oligomers) components than commercial MHA 88 product.

EXAMPLE 6

Determination of the viscosities according to "Cannon Fenske"

The kinematic viscosities were determined, as can be seen in FIGS. 8 to 11, using a viscosimeter of the Cannon Fenske opaque type according to the ISO 3105-1976 method as a function of the temperature for the following MHA qualities:

MHA distillate produced according to Example 4, Test 1, and storage at 25° C. for >230 days according to Example 5 corresponding to curve 1 in FIG. 8, viscosity (25° C.): 402 mm$^2$/s MHA distillate freshly produced according to Example 4, Test 4, corresponding to curve 2 in FIG. 8, viscosity (25° C.): 555 mm$^2$/s MHA distillate freshly produced according to Example 4, Test 9, corresponding to curve 3 in FIG. 8, viscosity (25° C.): 717 mm$^2$/s MHA 88 freshly produced according to Example 4, Test 5, corresponding to curve 4 in FIG. 9, viscosity (25° C.): 50 mm$^2$/s MHA 88, commercial product Alimet™ (NOVUS), corresponding to curve 5 in FIG. 9, viscosity (25° C.): 61 mm$^2$/s MHA 88, commercial product Rhodimet AT 88™ (Rhone Poulenc), corresponding to curve 6 in FIG. 9, viscosity (25° C.): 122 mm$^2$/s MHA78+10 MHA-NH$_4$ freshly produced according to Example 4, Test 7, corresponding to curve 7 in FIG. 10, viscosity (25° C.): 74 mm$^2$/s MHA 78+10 MHA-NH$_4$ produced according to Example 4, Test 7, and storage at 40° C. for 30 days according to Example 5, corresponding to curve 8 in FIG. 10, viscosity (25° C.): 79 mm$^2$/s MHA 69+19 MHA-NH$_4$ freshly produced according to Example 4, Test 8, corresponding to curve 9 in FIG. 10, viscosity (25° C.): 96 mm$^2$/s MHA 69+19 MHA-NH$_4$ produced according to Example 4, Test 8, and storage at 40° C. for 30 days according to Example 5, corresponding to curve 10 in FIG. 10, viscosity (25° C.): 100 mm$^2$/s MHA 78+10 Met produced according to Example 4, Test 3, and storage at 25° C. for >230 days according to Example 5, corresponding to curve 11 in FIG. 11, viscosity (25° C.): 113 mm$^2$/s MHA 78+10 Met freshly produced according to Example 4, Test 6, corresponding to curve 12 in FIG. 11, viscosity (25° C.): 122 mm$^2$/s As a comparison of the viscosity values at 25° C. shows, the viscosities of the highly concentrated MHA's are distinctly greater than those of the other MHA formulations. The longer storage induces a drop in the viscosities (see FIGS. 8 to 11).

MHA 88 from freshly distilled high concentrate has by far the most favorable viscosity value of 50 mm$^2$/s, which is also below the viscosity range of 61–122 mm$^2$/s of the commercial product (see FIG. 9).

The viscosities of the (MHA+MHA-NH$_4$) mixtures are at the lower edge to the middle of the viscosity range (see FIG. 10) and those of the (MHA+Met) mixtures on the upper edge of the viscosity range of the commercial product (see FIG. 11) and are thus comparable in this respect to the commercial products.

EXAMPLE 7

MHA regeneration from the bottom product of the distillation

Test 1

14.33 g (0.095 mol) 65% by weight $H_2SO_4$ were placed in a 100 ml three-neck flask with reflux condenser, internal thermometer and magnetic stirrer at 25° C. and 13.43 g (0.1 mol) 97.7% 4-methylthio-2-hydroxybutyric-acid nitrile (MMP-cyanohydrin) was added dropwise under agitation within 5 min. The reaction mixture was agitated 60 min further at 50° C. and the sulfuric-acid MHA-amide solution produced thereby subsequently mixed with 3.73 g (0.025 mol) bottom product from the MHA distillation according to Example 2, Test 1, and with 17.59 g water. The homogeneous solution with a content of 38% by weight MHA total was heated within 15 min to 108° C. to a boil and agitated another 105 min at this temperature. The analytically determined composition of the solution varied with time as follows:

| Time (min) | MHA amide (molar %) | MHA monomer (molar %) | DIM + OLI (molar %) |
| --- | --- | --- | --- |
| 15 | 5.2 | 60.0 | 34.8 after heating |
| 30 | 2.0 | 69.7 | 28.3 |
| 60 | 0.5 | 81.2 | 18.3 |
| 90 | 0 | 83.9 | 16.1 |
| 120 | 0 | 88.6 | 11.4 |

Test 2

60.0 g (0.15 mol) 37.4% by weight MHA hydrolyzate (with 0.15 mol MHA total, 0.15 mol $NH_4HSO_4$) which had been produced by sulfuric-acid hydrolysis of 4-methylthio-2-butyric-acid nitrile according to DE-OS 19524054, Example 4, was mixed in a 100 ml three-neck flask with reflux condenser, internal thermometer and magnetic stirrer with 5.6 g (0.037 mol) bottom product from the MHA distillation according to Example 2, Test 1, and with 8.2 g water. The homogeneous solution with a content of 38% by weight MHA total was heated within 20 min to 106° C. to a boil and agitated another 70 min at this temperature. The analytically determined composition of the solution varied with time as follows:

| Time (min) | MHA monomer (molar %) | DIM + OLI (molar %) |
| --- | --- | --- |
| 0 | 79.6 | 20.4 before heating |
| 25 | 86.7 | 13.3 |
| 35 | 88.6 | 11.4 |
| 60 | 91.3 | 8.7 |
| 90 | 95.8 | 4.2 |

Test 3

16.74 g (0.111 mol) bottom product from the MHA distillation according to Example 2, Test 1, was mixed in a 250 ml laboratory autoclave with glass tray, magnetic stirrer and internal thermometer with 27.32 g water and 0.44 g $H_2SO_4$ (4.5 mmol). The mixture was heated in the closed autoclave within 20 min to an internal temperature of 130° C. and agitated 90 min longer at this temperature and 3.5 bar pressure. After having cooled off rapidly to approximately 25° C., the reaction solution was analyzed. The composition of the solution had changed as follows:

| Time (min) | MHA monomer (molar %) | DIM + OLI (molar %) |
| --- | --- | --- |
| 0 | 14.0 | 86.0 before heating |
| 110 | 92.8 | 7.2 |

Test 4

16.74 g (0.111 mol) bottom product from the MHA distillation according to Example 2, Test 1 were mixed in a 250 ml laboratory autoclave with glass insert, magnetic stirrer and internal thermometer with 27.32 g water and 0.62 ml ion exchanger Amberlyst 15™ (Rohm & Hass, 1.8 eq $SO_3H/l$). The mixture was heated in the closed autoclave within 45 min to an internal temperature of 124° C. and agitated 120 min further at this temperature and a pressure of 2 bar. After a rapid cooling off to approximately 25° C. and depositing from the ion exchanger, the reaction solution was analyzed. The composition of the solution had changed as follows:

| Time (min) | MHA monomer (molar %) | DIM + OLI (molar %) |
| --- | --- | --- |
| 0 | 14.0 | 86.0 before heating |
| 165 | 87.7 | 12.3 |

What is claimed is:

1. A method for obtaining 2-hydroxy-4-methylthiobutyric acid (MHA) which is stable in storage, comprising:

distilling a highly-concentrated liquid MHA containing >95% by weight monomeric and oligomeric components of MHA for an average residence time of the MHA between 1 and $1 \times 10^4$ s, under reduced pressure of between $1 \times 10^{-3}$ and $5 \times 10^4$ Pa, at a temperature in a range between 40° and 200° C., at which the monomeric MHA is converted into a gaseous state for a time period which is sufficiently short that formation of significant by-product components is avoided.

2. The method according to claim 1, comprising obtaining the highly-concentrated liquid MHA as an educt by previous evaporation of any non-highly-concentrated MHA.

3. The method according to claim 2, comprising obtaining MHA as product having a stability in storage greater by a factor of 1.3 to about 2.5 than a stability in storage of the educt used with comparable water content, wherein the stability in storage is determined by comparing the MHA dimer and oligomer content of the product or educt with comparable water content which is adjusted in the equilibrium state.

4. The method according to claim 1, comprising obtaining the MHA as a solid, at least partially crystalline product.

5. The method according to claim 1, comprising obtaining an MHA product having an iodine color index in a range between 0 and <20.

6. The method according to claim 1, wherein apparatus in which the average residence time of the MHA in the distillation is between 1 and $1 \times 10^4$s comprises short-path distillation units.

7. The method according to claim 1, comprising obtaining MHA which is essentially free of MHA oligomers.

8. The method according to claim 1, comprising obtaining MHA with an oligomer content of less than 5% by weight at an exit of an evaporator.

9. The method according to claim 1, comprising obtaining bottom products in the MHA distillation which comprise MHA monomers, dimers and oligomers that are fed to a regeneration stage wherein the dimer and oligomer content is reduced by a hydrolysis step to values of ≦30 molar %, preferably ≦20 molar %, and especially ≦10 molar % relative to MHA total.

10. The method according to claim 9, comprising adding at least one member selected from the group consisting of mineral acids, mineral acid salts, MHA and acidic ion exchangers in the hydrolysis step.

11. The method according to claim 10, comprising adding at least one member selected from the group consisting of the mineral acids $H_2SO_4$, HCl, $H_3PO_4$ and ammonium salts thereof.

12. The method according to claim 10, comprising carrying out hydrolysis of the bottom products of the MHA distillation simultaneously with hydrolysis of MHA amide.

* * * * *